(12) United States Patent
Grady et al.

(10) Patent No.: US 6,638,909 B1
(45) Date of Patent: Oct. 28, 2003

(54) WOUND HEALING COMPOSITIONS CONTAINING ALPHA-1-ANTITRYPSIN

(75) Inventors: Michael W. Grady, Menston (GB); Stephen Bloor, Preston (GB); Peter J. Doyle, Tullibody (GB)

(73) Assignee: Ethicon, Inc., Somerville, NJ (US)

( * ) Notice: Subject to any disclaimer, the term of this patent is extended or adjusted under 35 U.S.C. 154(b) by 822 days.

(21) Appl. No.: 08/957,654

(22) Filed: Oct. 24, 1997

(51) Int. Cl.[7] .................. A61K 38/17; A61K 38/57
(52) U.S. Cl. .......................... 514/8; 514/21
(58) Field of Search .................. 530/350, 380, 530/386, 392, 395; 514/2, 8, 12, 21

(56) References Cited

U.S. PATENT DOCUMENTS

| 4,377,572 A | * | 3/1983 | Schwarz et al. | 514/2 |
| 4,829,052 A | * | 5/1989 | Glover et al. | 514/12 |
| 5,134,119 A | * | 7/1992 | Lezdey et al. | 514/18 |
| 5,202,118 A | * | 4/1993 | Gillis et al. | 424/85.2 |

FOREIGN PATENT DOCUMENTS

| EP | 097 274 | 1/1984 |
| EP | 103 409 | 3/1984 |
| EP | 114 777 | 8/1984 |
| EP | 139 383 | 5/1985 |
| EP | 169 114 | 1/1986 |
| EP | 173 619 | 3/1986 |
| EP | 067 293 | 6/1986 |
| EP | 222 726 | 5/1987 |
| EP | 224 811 | 6/1987 |
| EP | 253 690 | 1/1988 |
| EP | 298 807 | 1/1989 |
| EP | 304 971 | 3/1989 |
| EP | 149 872 | 5/1989 |
| EP | 319 944 | 6/1989 |
| EP | 127 535 | 1/1990 |

(List continued on next page.)

OTHER PUBLICATIONS

The Journal of Investigative Dermatology—Rao et al. vol. 105 Oct. 1, 1995, pp. 572–578.

Primary Examiner—Jeffrey E. Russel

(57) ABSTRACT

The invention provides the use of alpha-1-antitrypsin for the preparation of a composition for the treatment of a chronic wound, such as a pressure sore or a venous ulcer. The composition is preferably a wound dressing composition, such as an ointment for topical application.

6 Claims, 2 Drawing Sheets

FOREIGN PATENT DOCUMENTS

| | | |
|---|---|---|
| EP | 414 605 | 2/1991 |
| EP | 420 600 | 4/1991 |
| EP | 436 086 | 7/1991 |
| EP | 137 633 | 12/1991 |
| EP | 473 502 | 3/1992 |
| EP | 171 142 | 7/1992 |
| EP | 221 426 | 8/1992 |
| EP | 282 363 | 9/1992 |
| EP | 218 090 | 12/1992 |
| EP | 288 841 | 12/1992 |
| EP | 562 863 | 9/1993 |
| EP | 566 158 | 10/1993 |
| EP | 155 188 | 12/1993 |
| EP | 164 556 | 3/1994 |
| EP | 284 044 | 3/1994 |
| EP | 432 117 | 6/1994 |
| EP | 480 906 | 4/1995 |
| EP | 648 838 | 4/1995 |
| EP | 698 615 | 2/1996 |
| EP | 717 049 | 6/1996 |
| GB | 2 150 433 | 7/1985 |
| GB | 2 239 315 | 1/1994 |
| WO | 88/00239 | * 1/1988 |
| WO | WO 89 11285 | 11/1989 |
| WO | WO 91 07166 | 5/1991 |
| WO | WO 91 07490 | 5/1991 |
| WO | WO 91 07983 | 6/1991 |
| WO | WO 92 06706 | 4/1992 |
| WO | WO 92 19730 | 11/1992 |
| WO | WO 93 03769 | 3/1993 |
| WO | WO 93 13795 | 7/1993 |
| WO | WO 94 07525 | 4/1994 |
| WO | WO 94 13318 | 6/1994 |
| WO | WO 94 16073 | 7/1994 |
| WO | WO 94 26781 | 11/1994 |
| WO | WO 94 26896 | 11/1994 |
| WO | WO 95 11987 | 5/1995 |
| WO | WO 95 24428 | 9/1995 |
| WO | WO 95 35306 | 12/1995 |
| WO | WO 96 10638 | 4/1996 |
| WO | WO 96 28008 | 9/1996 |
| WO | WO 96 29988 | 10/1996 |
| WO | WO 96 40224 | 12/1996 |
| WO | WO 97 09350 | 3/1997 |

* cited by examiner

WOUND HEALING COMPOSITIONS CONTAINING ALPHA-1-ANTITRYPSIN

The present invention relates to the use of alpha-1-antitrypsin (AAT) for the preparation of compositions for the treatment of chronic wounds.

alpha-1-antitrypsin (AAT), also known as alpha-1-proteinase inhibitor or serpin, is a mammalian polypeptide having a molecular weight of approximately 54 kDa. It is a potent fluid phase inhibitor of serine proteases, and forms a tightly bound, stoichiomedric complex with elastase. It can be inactivated by cleavage within its reactive centre. For example, neutrophil collagenase (MMP8) is know to degrade and inactivate AAT.

AAT deficiency is a congenital disorder that is principally associated with liver disease in children and emphysema in young adulthood. It is thought that AAT deficiency results in loss of protection in the lung against neutrophil elastase, resulting in breakdown of the architecture of the lung. AAT has been administered in intravenous and aerosol formats for the treatment of pulmonary emphysema.

It is an object of the present invention to provide improved compositions for the treatment of chronic wounds, such as decubitis ulcers, pressure sores and venous ulcers.

The present invention provides the use of alpha-1-antitrypsin for the preparation of a composition for the treatment of a chronic wound.

Preferably, the composition is a wound dressing composition. That to say, the composition is preferably a liquid, semi-solid or solid composition for application directly to the surface of a wound, or the composition is applied to the surface of, or incorporated into, a solid wound contacting layer such as a wound dressing gauze or film. More preferably, the wound dressing composition is a fluid or a gel comprising from 100 ng to 10 mg/ml, preferably 10 $\mu$g to 1 mg/ml of AAT in combination with conventional pharmaceutical excipients for topical application to a wound. Suitable carriers include: Hydrogels containing cellulose derivatives, including hydroxyethyl cellulose, hydroxymethyl cellulose, carboxymethyl cellulose, hydroxypropylmethyl cellulose and mixtures thereof; and hydrogels containing polyacrylic acid (Carbopols). Suitable carriers also include creams/ointments used for topical pharmaceutical preparations, e.g. creams based on cetomacrogol emulsifying ointment. The above carriers may include alginate (as a thickener or stimulant), preservatives such as benzyl alcohol, buffers to control pH such as disodium hydrogen phosphate/sodium dihydrogen phosphate, agents to adjust osmolarity such as sodium chloride, and stabilisers such as EDTA.

Alternatively, the wound dressing composition may be a slow release solid composition, in which the AAT is dispersed in a slow release solid matrix such as a matrix of alginate, collagen, or a synthetic bioabsorbable polymer. Preferably, the wound dressing composition is sterile.

Preferably, the chronic wound is selected from the group consisting of venous ulcers, pressure sores, decubitis ulcers, diabetic ulcers and chronic ulcers of unknown etiology. Preferably, the chronic wound is not a periodontal disease condition.

It is to be understood that the term "alpha-1-antitrypsin" as used herein encompasses all naturally occurring polymorphs of AAT. It also encompasses functional fragments of AAT, chimeric proteins comprising AAT or functional fragments thereof, homologs obtained by analogous substitution of one or more amino acids of AAT, and species homologs. Preferably, the AAT is a product of recombinant DNA technology, and more preferably the AAT is a product of transgenic technology. For example, the gene coding for AAT can be inserted into a mammalian gene encoding a milk whey protein in such a way that the DNA sequence is expressed in the mammary gland, as described in WO88/00239.

Without wishing to be bound by any theory, it is thought that the AAT improves the healing of chronic wounds by inhibiting human neutrophil elastase present in the wound. The healing of such wounds is determined by a complex balance between tissue formation and tissue destruction, and it appears that inhibition of neutrophil elastase by AAT shifts the balance in favour of wound healing.

In another aspect, the present invention provides a method for the treatment of chronic wounds as specified above, the method comprising administering a therapeutically effective amount of AAT to the patient. Preferably, the AAT is administered topically, more preferably in a topical composition as described above.

BRIEF DESCRIPTION OF THE DRAWINGS

The present invention now be described further with reference to the accompanying drawings, in which.

PROCEDURE 1

Figure 1:
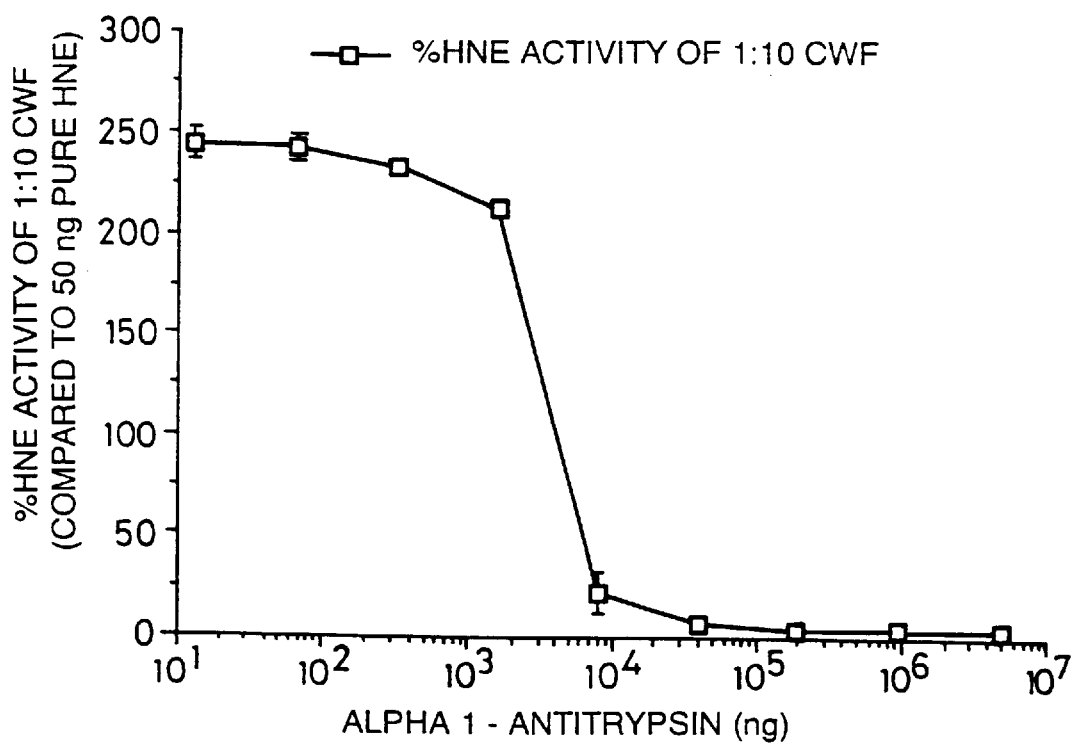
FIG. 1 shows the effect of AAT concentration on the activity of human neutrophil elastase in chronic wound fluid as a function of AAT concentration.

AAT is obtained from PPL Therapeutics, East Mains, Ormiston, East Lovian, EH35 5NG, Scotland. The formulation is produced by transgenic technology by inserting the human gene for the AAT protein into the milk protein gene sequence of sheep. Upon lactation the AAT is purified from the milk and stored as a freeze dried pure protein. Details of the transgenic production method are given in WO88/00239.

AAT from human plasma is also obtainable commercially from Sigma Chemical Company as product A9024.

PROCEDURE 2

The effect of AAT on the activity of human neutrophil elastase (HNE) is studied as follows.

Elastase substrate (31.1 mg) supplied by Calbiochem Inc. under catalog reference 324696 is reconstituted in 2 mil of pure DMSO in order to solubilise the substrate, and 8 ml of buffer (100 mM Tris-HCl, pH 7.5, 0.5M NaCl, containing 0.1% Triton®) is added to give a final substrate stock concentration of 5 mM. Purified human neutrophil elastase (100 $\mu$mg) is supplied by Calbiochem Inc. under catalog reference 324681 is reconstituted in 1 ml of buffer (100 mM Tris-HCl, pH 7.5, 0.5M NaCl, containing 0.1% Triton®).

The neutrophil elastase activity of 50 ng of human neutrophil elastase HNE was measured using an elastase substrate concentration of 1 mM and determined over an assay period of 1 hr at 25° C. The total assay volume is 100 $\mu$l. The change in absorbance of the substrate (Meo-Suc-Ala-Pro-Val-pNa) was monitored at 410 nm on a 96 well plate. The appropriate substrate blanks are included with each experiment. The ability of the purified neutrophil elastase at 50 ng to hydrolyse the substrate (1 mM) at varying concentrations was tested in the presence or absence of 20 μls of AAT (0.5 ng–50 mg/ml). The percentage inhibition was determined by comparison with a positive control containing elastase and substrate but no AAT, and with a negative control containing substrate but no elastase or AAT.

Figure 2:
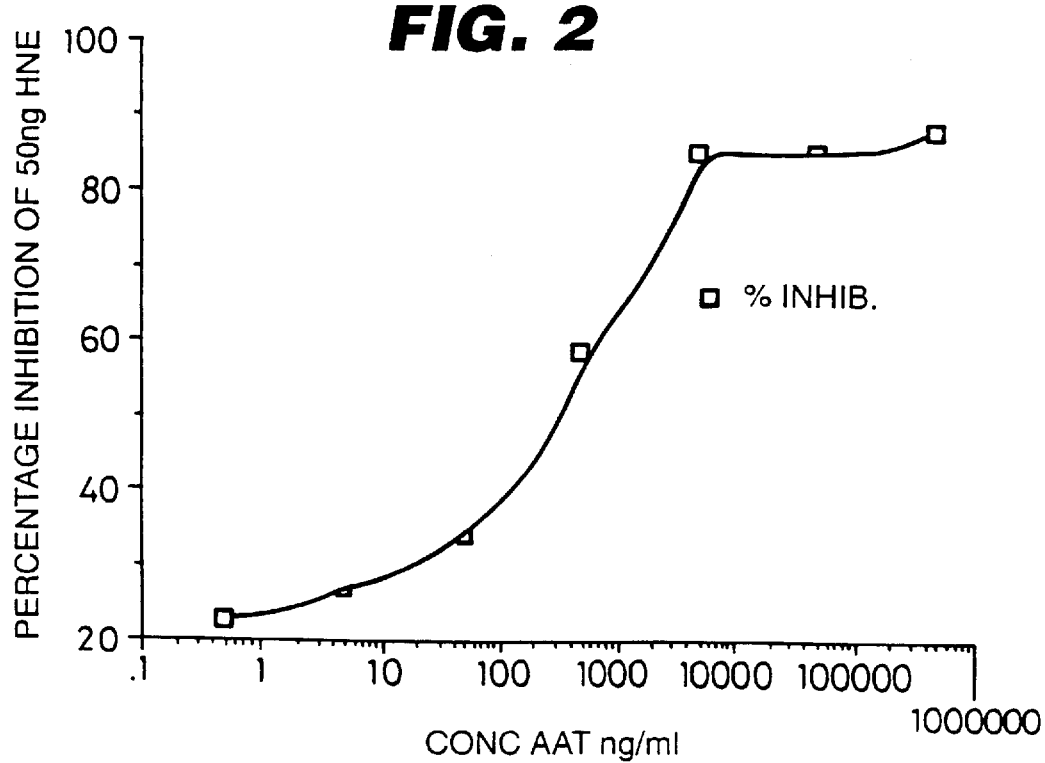
FIG. 2 shows inhibition of human neutrophil elastase by AAT as a function of AAT concentration.

The results of the study on pure HNE are shown in FIG. 2. It can be seen that concentrations of AAT above about 1000 ng/ml substantially inhibit the activity of the HNE.

Likewise, it can be seen from FIG. 1 that the activity of HNE present in chronic wound fluid is strongly inhibited by AAT at concentrations above about 2000 ng/ml. In FIG. 1, the x-axis shows the concentration of AAT in ng/ml, and the y-axis shows the elastase activity of a sample of human wound fluid relative to 50 ng/ml of pure HNE.

PROCEDURE 3

The effect of AAT on the viability of cells similar to those found in chronic wounds was assessed as follows.

The basic method is described by Borenfreund and Peurner in *Cancer Letters*; vol. 34; pages 243–248 (1987), and by Borenfreund et al. in *Toxicology in vitro*; vol. 2; pages 1–6 (1988). The method comprises challenging selected cells with the compound to be tested for 3 days, and then determining the number of live cells remaining.

Rat wound fibroblast (RWF) cells of L929 fibroblast cells were removed from tissue culture flasks by trypsination, and counted. The cells were suspended in Dulbecco's Modified Eagle's Medium (DMEM) to give a cell density of $5 \times 10^4$ cells/ml. Aliqeuots of 100 μl, each containing 5000 cells were then dispensed into wells of a 96 well plate.

Samples of AAT were dissolved in DMEM at concentrations of 500 pg/ml to 5 mg/ml, and 100 μl aliquots of these solutions were added to the wells containing the fibroblast cells. Four wells were tested for each AAT concentration. The plates were incubated at 37° C., 5% $CO_2$, humidified atmospheres, for 3 days.

The number of active cells remaining in each well was then determined by the neutral red assay, as described in the references above. Briefly, the assay measures the uptake of the dye neutral red by viable active cells. The dye becomes localized in the lysosomes and is extracted from the cells using an acidic solution. The absorbance of the extracted dye is read at 540 nm and correlates with the number of active cells.

Figure 3:
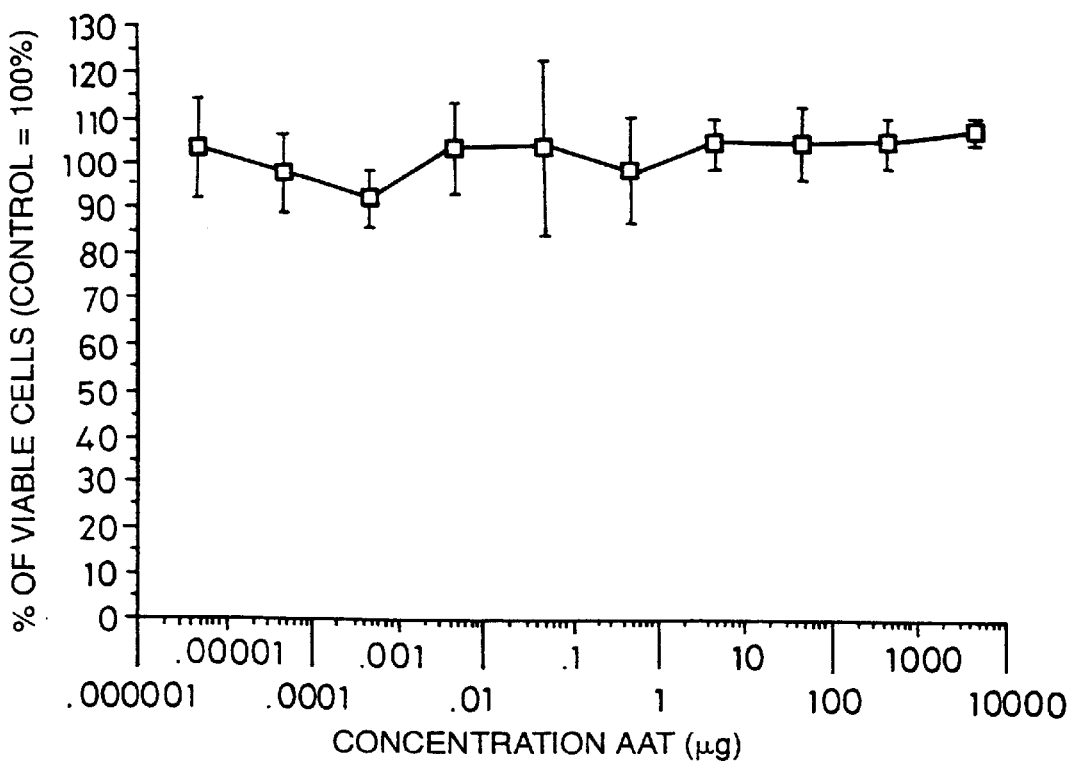
FIG. 3 shows the effect of AAT on the cell viability of rat wound fibroblast (RWF) cells as a function of AAT concentration.
Figure 4:
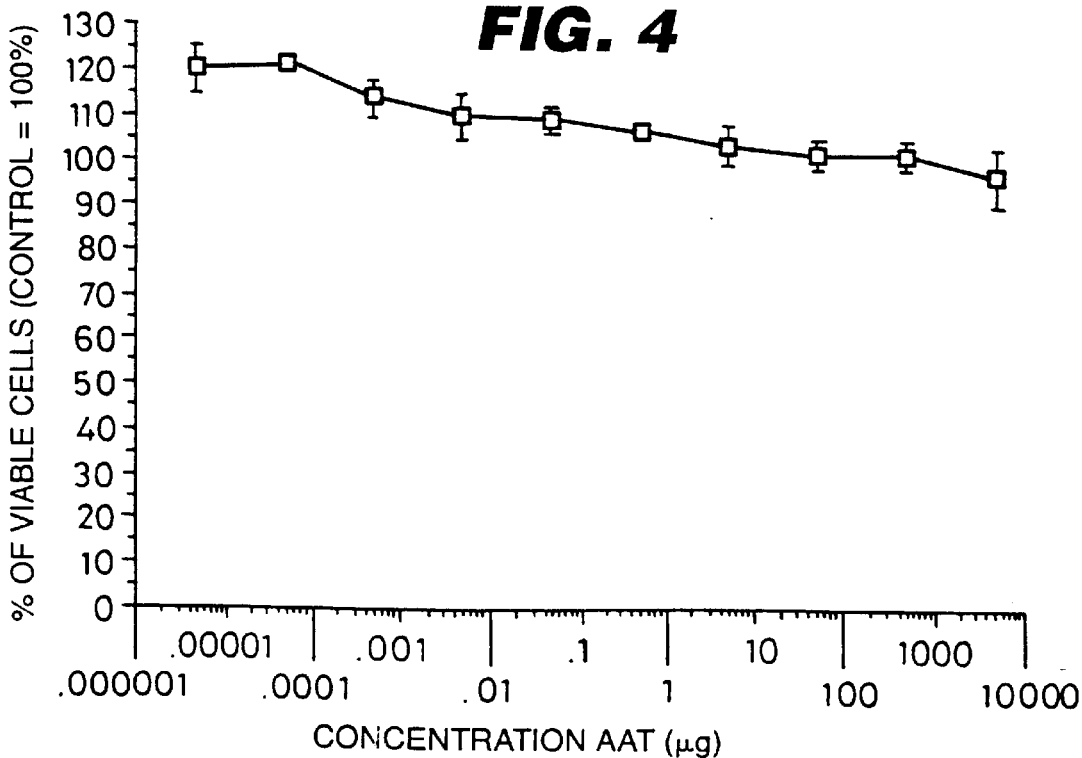
FIG. 4 shows the effect of AAT on the viability of L929 fibroblast cells as a function of AAT concentration.

The results shown in FIGS. 3 and 4 illustrate that AAT has little or no effect on the viability of the cells tested, even at quite high AAT concentrations. The low cytotoxicity of the AAT indicates that it is suitable for topical application to chronic wounds.

EXAMPLE 1

An ointment containing AAT and suitable for topical adminstration to a venous ulcer, decubitus ulcer or pressure sore is prepared by mixing the following ingredients in the following percentages by weight:

| Freeze-dried AAT | 0.001% |
| Hydroxyethyl Cellulose | 0.35% |
| Carboxymethyl Cellulose | 3.00% |
| Propylene Glycol | 25.00 g |
| Sodium Chloride | 0.30% |
| Distilled Water qs to | 100% |

The ointment is entirely wound-friendly and non-cytotoxic, and can be applied to the chronic wound surface at regular intervals until wound healing is achieved.

Many other embodiments of the present invention falling within the scope of the accompanying claims will be apparent to the skilled reader.

What is claimed is:

1. A method of treating a wound comprising applying to the wound, externally, a therapeutically effective amount of alpha-1-antitrypsin, and wherein the wound is selected from the group consisting of venous ulcers, pressure sores, decubitis ulcers and diabetic ulcers.

2. The method of claim 1, wherein the alpha-1-antitrypsin is supplied to the wound in a wound dressing composition.

3. The method of claim 2, wherein the wound dressing composition is a fluid or a gel comprising from 10 to 1000 μg/ml of alpha-1-antitrypsin in combination with one or more pharmaceutical excipients for topical application to a wound.

4. The method of claim 1, wherein the alpha-1-antitrypsin is a product of transgenic technology.

5. The method of claim 1, wherein the alpha-1-antitrypsin inhibits the activity of human neutrophil elastase in the wound.

6. A wound dressing composition for the treatment of wounds selected from the group consisting of venous ulcers, pressure sores, decubitus ulcers and diabetic ulcers comprising a therapeutically effective amount of alpha-1-antitrypsin, wherein the wound dressing composition is a fluid or a gel comprising from 10 to 1000 μg/ml of alpha-1-antitrypsin in combination with one or more pharmaceutical excipients for topical application to a wound.

* * * * *